United States Patent [19]

Iwata et al.

[11] Patent Number: 4,708,948
[45] Date of Patent: Nov. 24, 1987

[54] SUBSTANTIALLY PURIFIED TUMOR GROWTH INHIBITORY FACTOR

[75] Inventors: Kenneth K. Iwata, Westbury, N.Y.; Charlotte M. Fryling, Arlington, Va.; George J. Todaro, Seattle, Wash.

[73] Assignee: The United States of America as represented by the Department of Health and Human Services, Washington, D.C.

[21] Appl. No.: 602,520

[22] Filed: Apr. 20, 1984

[51] Int. Cl.$^4$ ................... A61K 37/00; C07K 15/00; C12Q 1/18; C12P 21/00
[52] U.S. Cl. .......................................... 514/2; 435/32; 435/68; 435/948; 530/300; 530/350; 530/399; 530/828; 424/85
[58] Field of Search ................ 435/32, 68, 70, 240, 435/241, 802, 811, 948; 260/112; 424/85, 177; 530/300, 350, 351, 399, 828; 514/2, 21; 436/63, 64

[56] References Cited

U.S. PATENT DOCUMENTS 4,261,976  4/1981  Isselbacher ........................... 424/95

FOREIGN PATENT DOCUMENTS 0100641  2/1984  European Pat. Off. .

OTHER PUBLICATIONS

Matthews, N. et al., Br. J. Cancer, 42(3):416–422(1980).
Funkhouser, W. K. et al., Surg. Forum, 35:394–396(1984).
Dittmer, John E., "Suppression of Tumor Cell Growth in vitro by a Bone Marrow Factor", Cancer Research, vol. 44, (Mar. 1984) pp. 900–903.
Immunology, vol. 44, No. 1, (Sep. 1981) pp. 135–142, "Production of an Anti-Tumor Cytotoxin by Human Monocytes", Matthews et al.
Todaro, et al.; Tumor Cell Heterogeneity; 1982; pp. 205–224, vol. 4.
Todaro, et al., "Transforming Growth Factors Produced by Certain Human Tumor Cells; Polypeptides, P.N.A.S.", Sep. 1980; pp. 5258–5262; vol. 77.
Holley, et al.; Activity of Kidney Epithelial Cell Growth Inhibitor on Lung and Mammary Cells; Feb. 1983; pp. 141–147; vol. 7, Cell Biol.
Holley et al.; Preparation and Properties of a Growth Inhibitor Produced by Kidney Epithelial Cells; Jul. 1983; pp. 525–526; vol. 7, Cell Biol.
McMahon et al.; "Purification & Properties of a Rat Liver Protein that Specifically Inhibits Proliferation . . . ." P.N.A.S. Jan. 82; vol. 79, pp. 456–460.
Savage et al.,; Epidermal Growth Factor and a New Derivative; 1972; pp. 7609–7611; vol. 247, J. Biological Chemistry.
Greenwood et al., The Preparation of 131-I-Labelled Human Growth Hormone of High Specific Radioactivity, Biochem J., pp. 114–123, vol. 89 (1963).
De Larco et al., Sarcoma Growth Factor from Mouse Sarcoma Virus Transformed Cells, pp. 3685–3690, vol. 255, (1980) J. Biol. Chem.
Holley et al., Purification of Kidney Epithelial Cell Growth Inhibitors, pp. 5989–5992, vol. 77, (1980), Proc. Natl. Acad. Sci.
Iwata et al., Isolation and Characterization of Human Tumor Cell Inhibitory Factors, (1983), Fed. Proc.
Iwata et al., Methods for Rapid Microanalysis of Transforming Factors (TGFs) NAD Cell Inhibitory Factors, (1982), J. Cell. Biochem.

Primary Examiner—Margaret Moskowitz
Attorney, Agent, or Firm—Holman & Stern

[57] ABSTRACT

A substantially purified substance having the property of inhibiting tumor cell growth without inhibiting the growth of normal human cells and without having antiviral effect, further having the properties of: (a) ranging from about 3,500 to 45,000 daltons in molecular weight; (b) being heat stable at about 56° C. when exposed for about 30 minutes; (c) possessing isoelectric point ranging from pI 4–8; and (d) eluting on high pressure liquid chromatography at about 10–35% of 2-propanol or about 25–50% of acetonitrile gradient, has been disclosed. The substance has utility as an antitumor or antineoplastic agent. The substance may also be useful as an index or tumorgenic activity in an organism. The mitogenic and growth stimulatory activity possessed by the substance of the present invention may be useful in wound healing and treating burn-victims.

2 Claims, 10 Drawing Figures

A = UNTREATED  B = TREATED WITH 570 µg TIF-1

A – UNTREATED
B – TREATED WITH 64 μg/ml OF TIF-2

SUBSTANTIALLY PURIFIED TUMOR GROWTH INHIBITORY FACTOR

BACKGROUND OF THE INVENTION

1. Technical Field

The present invention relates to substantially purified tumor growth inhibiting factor (TIF). More particularly, the present invention is directed to substantially purified polypeptide factors capable of inhibiting the growth of certain cancer cells without adversely affecting the growth of certain normal human cells.

2. Discussion of the Prior Art

A wide variety of tumor growth factors (TGF) and growth inhibitory substances are known in the art. Holley et al., Proc. Natl. Acad. Sci. USA 77:5989, 1980 and Holley et al. Cell Biol. Int. Reports 7, 525–526 (1983), have reported the isolation of a potent growth inhibitor from African green monkey kidney BSC-1 cells, which was found to inhibit the growth of the producer cell as well as human mammary tumor cells and normal human mammary cells. McMahon et al. (1982) Proc. Natl. Acad. Sci. USA 79, 456–460 have purified a 26,000 $M_r$ (relative molecular weight) inhibitor of cell proliferation from rat liver which affects nonmalignant rat liver cells, but does not affect the proliferation of malignant rat liver cells. Other growth inhibitors have been found in cultured chick spinal cord cells (Kagen, et al (1978) Experimental Neurology 58, 347–360; Harrington, et al (1980) Proc. Natl. Acad. Sci. USA 77, 423–427; and Steck, et al (1979) J. Cell Biol. 83, 562–575).

Bichel (1971) Nature 231, 449–450 reported that aspiration of most of the tumor from mice bearing ascites tumors at a plateau of growth was followed by a marked increase in growth of the remaining tumor cells. Injection of cell-free ascites, obtained from mice bearing fully developed ascites tumors, into mice with growing ascites tumors resulted in a pronounced inhibition of ascites growth. Bichel, supra, also observed that two surgically joined mice (parabiotic), one mouse with an advanced tumor and the other with an early tumor, resulted in a pronounced inhibition of growth of the early tumor. These observations Bichel (1970) Europ. J. Cancer 6, 291–296 and Bichel, supra, were explained by the existence of a diffusible inhibitory principle which circulated through the peritoneum of the parabiotic mice and was present in the cell-free ascites fluid produced by the fully developed ascites tumors. The nature of this inhibiting principle was not characterized, but the speculation was that the rate of growth of the ascites tumors depended upon the amount of tumor tissue present in the mouse and the amount of tumor tissue determining the amount of the inhibitory principle produced.

Todaro et al, Bristol-Myers Cancer Symposium 4:222–223, 1982, reported some properties of certain tumor cell growth inhibitory factors. Not only the observations made by Todaro et al, supra, were preliminary, based on partially purified preparations, but the TIFs of the present invention differ from those of the prior art in several fundamental respects:

(1) Whereas the TIFs of the prior art block TGF-dependent growth of normal cells, the TIFs of the present invention are noninhibitory to the TGF-dependent growth of normal cells.

(2) Whereas the prior art wondered whether there were different families or types of inhibitory factors, the present invention has in fact isolated, substantially purified and established at least two different kinds of TIFs not only distinct from the prior art but distinguishable from each other; and (3) Unlike the TIFs previously known, the TIFs of the present invention possess a novel mitogenic and human cell growth stimulating property.

SUMMARY OF THE INVENTION

It is, therefore, an object of the present invention to isolate, identify and characterize substantially pure human tumor cell growth inhibiting factors (TIFs).

It is a further object of the present invention to obtain substantially purified TIFs, other than interferon, which inhibit the growth of neoplastic human cells but do not inhibit the growth of normal human cells.

Another object of the present invention is to provide a TIF having the property of stimulating growth of normal human cells.

It is yet another object of the present invention to describe a method of preparing substantially purified TIFs.

A further object of the present invention is to prepare a pharmaceutical composition for inhibiting growth of neoplastic cells in mammals comprising an antiproliferative amount of TIF and a pharmaceutically acceptable carrier or adjuvant.

A still further object of the present invention is a method of inhibiting growth of tumor cells in mammals comprising administering an antiproliferative amount of TIF to a mammalian host to inhibit growth of said tumor cells.

A yet another object of the present invention is to employ the ratio of tumor inhibiting factor to transforming growth factor as a prognosticating index of tumor cell proliferation.

The growth stimulating and mitogenic property of the TIFs may be useful in the treatment of burns and other conditions where new cell growth is needed, e.g. wound healing.

Other objects and advantages of the present invention will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the accompanying drawings, wherein.

DETAILED DESCRIPTION OF THE INVENTION

Figure 1:
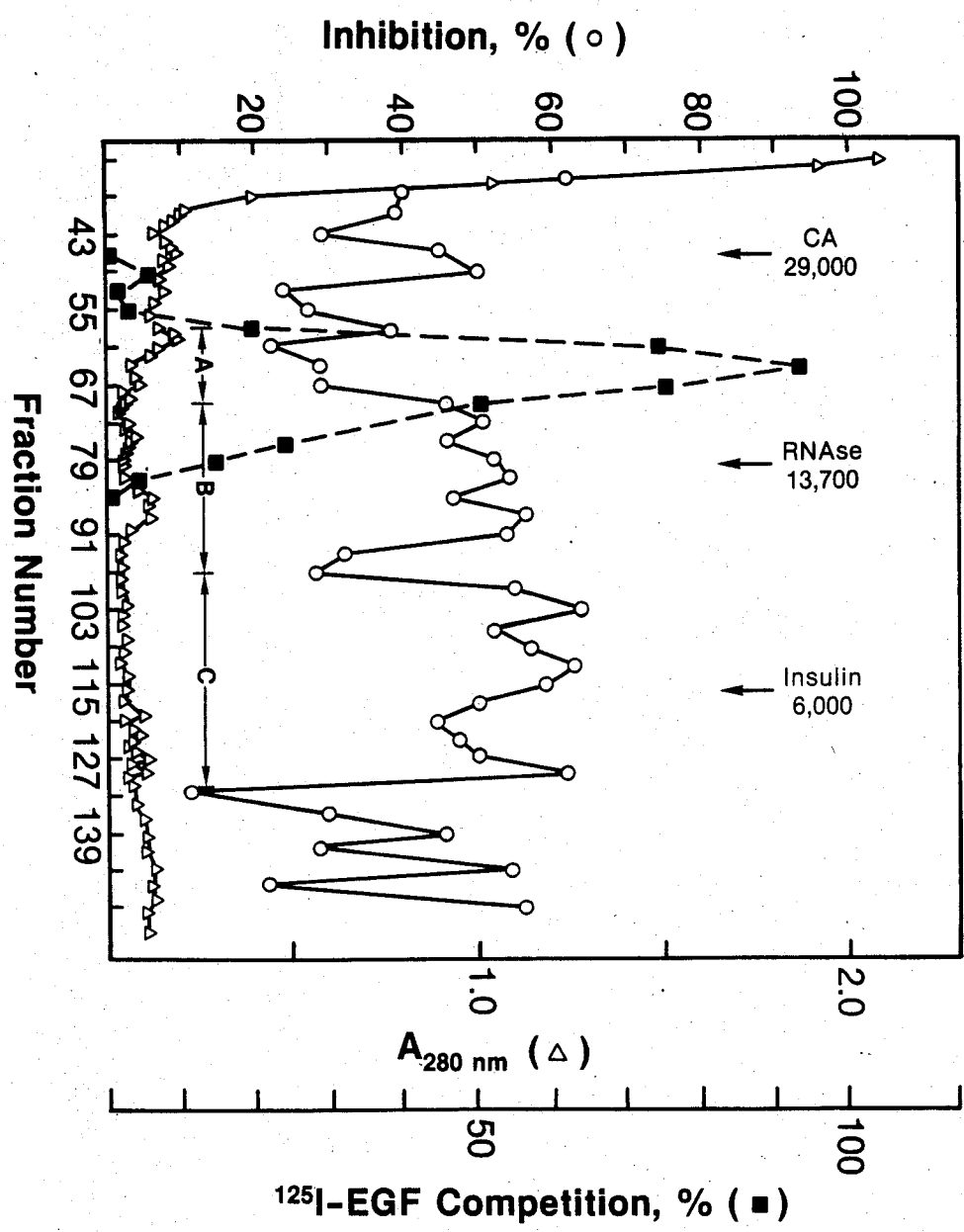
FIG. 1 shows the elution pattern on Bio-Gel P-100 chromatography of concentrated conditioned medium from human rhabdomyosarcoma cells A673.

Tumor inhibiting factors can be obtained from a variety of sources such as mammalian body fluids, e.g. urine, serum, plasma, and amniotic fluid; adult and fetal mammalian tissues, e.g. livers, heart, lung, spleen, muscle, brain, placenta, umbilical cords, kidneys, pancreas; conditioned media, e.g. normal and human cell conditioned media in tissue culture; extracts from tissue culture cells and the like.

Tumor inhibiting factors can be isolated and purified by using a variety of protocols including acid/ethanol extraction, gel permeation chromatography, ion exchange chromatography, high-performance liquid chromatography (HPLC) and the like.

Among the additives, carrier and/or adjuvants any suitable substance well known in the art could be used. Preferred substance may be physiological saline, aqueous solvents, fillers, preservatives, antimicrobial agents, sterilants and the like.

As the data provided herein below would show, the tumor growth inhibiting factors (TIFs) of the present invention are several classes of heat stable proteins of apparant molecular weight ranging from 3500–45,000 daltons with isoelectric points ranging from pI 4–8, prominent among which are TIF-1 and TIF-2. TIFs are somewhat hydrophobic eluting from a $C_{18}$ column on reverse phase high performance liquid chromatography at between 25–50% acetonitrile or between 10–35% 2-propanol. Some of the characteristics and properties of TIFs are described infra.

The term "substantially purified" means a preparation having better than 80% purity, preferably more than 90% pure and more preferably greater than 95% pure.

MATERIALS AND METHODS

It should be noted that although any suitable material and source of supply and method similar or equivalent to those described herein infra may be used, the following are preferred.

ISOLATION OF TUMOR INHIBITING FACTORS (TIF) FROM TISSUE EXTRACTION

Tissues were extracted with modifications of acid/ethanol extraction procedures described by Davoren, Biochem. Biophys. Acta. 63:150, (1962) and Roberts et al, Proc. Natl. Acad. Sci. USA. 77:3494 (1980), both of which are incorporated herein by reference. A solution of 375 ml of 95% (v/v) ethanol, 7.5 ml of concentrated HCL, 33 mg of phenylmethylsulfonyl fluoride (PMSF) and 1 ml of Aprotinin (10–20 trypsin inhibitor units (TIU) in 0.9% NaCl and 0.9% benzyl alcohol) was mixed with 192 ml of distilled water. Tissue was suspended in this solution (6 ml/gm of tissue), minced with scissors, and homogenized in a Sorvall Omni-mixer. After overnight extraction at 4° C., the mixture was centrifuged at 5000× g for 30 minutes and the pellet discarded. The extract was adjusted to pH 5.0 with concentrated ammonium hydroxide followed by the addition of 1 ml of 2 M ammonium acetate buffer, pH 5.2, per 100 ml extract. This extract was centrifuged at 5000×g for 30 minutes to remove precipitated material, which was discarded. Four volumes of cold anhydrous ether and two volumes of cold absolute ethanol were immediately added and the mixture was allowed to stand undisturbed at −20° C. for 48 hours. The resulting precipitate was allowed to settle and the majority of liquid siphoned off. The remaining suspension was centrifuged at 5000× g for 30 minutes and the pellet was saved. The pellet was dissolved in 1 M acetic acid and dialyzed extensively against 0.2 M acetic acid in Spectrapor tubing with a molecular weight cut off of 3500 (Spectrum Medical Industries, Los Angeles, Calif.). The material was stored at 4° C. in 1 M acetc acid or lyophilized.

Conditioned Media

Serum-free conditioned media was collected from a human rhabdomyosarcoma cell line, A673. Cells were grown to confluence on Corning 850 $cm^2$ roller bottles (Corning 25140) in 50 ml of Dulbecco's minimum essential medium (DMEM) supplemented with 10% fetal bovine serum (FBS). The monolayers were then rinsed twice with 50 ml of serum-free DMEM. Each roller bottle was incubated in 50 ml of serum-free Waymouth's medium (Meloy Labs, Inc.) for 8 hr. The medium was discarded and replaced with 50 ml of fresh, serum-free Waymouth's medium and the cells were incubated for 48 hr. The "conditioned media" were collected and replaced with 50 ml of fresh, serum-free Waymouth's medium for 48 hr. A total of three collections of conditioned media was made per confluent monolayer of A673 cells. The collected, conditioned media were then pooled and clarified by centrifugation on a Beckman CF-32 rotor at 32,000 rpm with a flow rate of 5 liters/hr. The clarified material was concentrated or an Amicon DC-10 hollow fiber filter (MW cutoff=5000) and concentrated 100-fold (e.g., 50 liters to 500 ml). The concentrated material was saved and the filter was washed with 200 ml of filtrate to remove residual factor. The concentrate and wash were pooled in Spectrophor 3 dialysis tubing (MW cutoff=3500) and dialyzed against 2 liters of 0.1 M acetic acid. The dialyzed material was centrifuged on a Beckman Type 35 rotor at 27,000 rpm for 1 hr. The pellet was discarded and the supernatant fluid was lyophilized.

Cell Cultures

Cell cultures were maintained at 37° C. in 75 $cm^2$ plastic tissue culture flasks (Falcon No. 3024) with Dulbecco's modification of Eagle's medium supplemented with 10% FBS (Gibco) with the exception of cell lines 3T3 2-2, 49 F, and Kirsten virus transformed normal rat kidney cells (KNRK) which require 10% calf serum. A673 is a human rhabdomyosarcoma. A549 is a human adenocarcinoma of the lung. HuF is a human foreskin fibroblast cell line, passage 10–25, in tissue culture provided by J. Levy, Cancer Research Institute, University of California, San Francisco. 3T3 2-2 is a clone of mouse NIH 3T3 cells provided by M. Wigler, Cold Spring Harbor Laboratories, N.Y.

Gel Permeation Chromatography

The lyophilized conditioned media (200–300 mg from 30–100 liters of conditioned media) were resuspended in 15–20 ml of 1 M acetic acid and applied to a column (5×82.5 cm) of Bio-Gel P-100 (100–200 mesh, polyacrylamide gel Bio-Rad), equilibrated and eluted with 1 M acetic acid at 4° C. Fractions (12.4 ml) were collected and a 2.5 µl aliquot was removed from every third fraction and assayed for TIF activity. A 100 µl aliquot was removed from every third fraction and assayed for TGF activity. The fractions containing growth modulating activity (TIFs and TGFs) were divided into three pools, A–C, (FIG. 1) and lyophilized.

Pool B was lyophilized for further purification on a Bio-Gel P-10 column. The lyophilized sample (20–40 mg) was dissolved in 5–7 ml of 1 M acetic acid and centrifuged at 4° C. for 30 min at 200× g to remove insoluble material. The supernatant was applied to a column (2.5×87 cm) of Bio-Gel P-10 (200–400 mesh, polyacrylamide gel, Bio-Rad) equilibrated, and eluted with 1 M acetic acid at 4° C. Fractions (4.6 ml) were collected and a 100 µl aliquot was removed from every third fraction and assayed for TIF activity.

Reverse-Phase High-Performance Liquid Chromatography (rp-HPLC)

The fractions containing the peak of TIF activity from the Bio-Gel P-10 column were combined. Typically, these were fractions 44–47. The material from the equivalent of 30–60 liters of conditioned media was used for each HPLC chromatogram. The combined Bio-Gel P-10 fractions were lyophilized and the residue was resuspended in 1 ml of 0.05% trifluoroacetic acid. This solution was centrifuged for 5 min at 1000× g to remove insoluble material. The supernatant was injected on a Waters µBondapak $C_{18}$ column (0.39×30 cm). IBM gradient liquid chromatography equipment (IBM LC/9533) was used. The column eluate was monitored with a variable wavelength u.v. detector (IBM LC/9523) set at 206 nm. Major peaks of absorbance at 206 nm were collected in fractions. Aliquots from each collected fraction were assayed for TIF or TGF activity.

Soft Agar Growth Inhibition Assay

Lyophilized samples to be tested were dissolved in complete growth medium (DMEM supplemented with 10% FBS) in a final volume of 1.4 ml containing 0.34% agar (Difco, Agar Noble) and $2 \times 10^4$ human lung carcinoma cells, A549. This soft agar suspension of treated cells was pipetted on a 2 ml base layer of 0.5% agar containing complete growth medium in 60 mm petri dishes (Falcon 3002). Plates were incubated at 37° C. for 3 weeks in a humidified 5% $CO_2$/95% air atmosphere. At 7 days, cultures were re-fed with 1.5 ml of 0.34% agar containing complete growth medium. Photomicrographic records of growth in soft agar were made at 2 and 3 weeks.

Tumor Inhibiting Factor Assay

Test cells ($3 \times 10^3$ cells/well) were subcultured on 96-well tissue culture plates (Nunc 167008) in 50 µl of complete medium. Human lung carcinoma cells, A549, required a seeding density of $4.5 \times 10^3$ cells per well. Aliquots from column fractions to be assayed for TIF activity were transferred to sterile 12×75 mm tubes (Falcon 2058) containing 50 µl of a 1 mg/ml solution of bovine serum albumin (BSA) (Sigma A-6003) in 1 M acetic acid and lyophilized. Immediately prior to the assay, the lyophilized sample was resuspended in 200 µl of complete medium. Fifty-µl aliquots of the resuspended sample were added to wells containing test cells. Each sample was assayed in triplicate. The cells were incubated for 72 hr at 37° C. in a humidified 5% $CO_2$/95% air atmosphere. At the end of this incubation period, each well was pulsed with 100 µl of complete medium containing 1 µCi/ml 5-[$^{125}$I]Iodo-2'-deoxyuridine ($^{125}$IUdR) (Amersham IM.355V) for 24 hr. The monolayers were washed once with wash buffer (Dulbecco's modified Eagle's medium containing 1 mg/ml BSA and 50 mM 2-is(2-hydroxyethyl)aminoethanesulfonic acid, pH 6.8), fixed for 10 minutes in absolute methanol, and air dried for 15 minutes. The $^{125}$IUdR incorporated by the cells was solubilized with 200 µl of 1 N NaOH and incubated for 20 min at 60° C. Solubilized $^{125}$IUdR incorporated by cells in each well was harvested using the Titertek Supernatant Collection System (Flow Laboratories, 78-210-05). The amount of cell growth is approximated by the extent of $^{125}$IUdR incorporated into the DNA of cells in the log phase of growth. Before the assay was harvested, each well was observed using a Leitz inverted microscope to visually note the amount of cell growth. Inhibition of cell growth observed under microscopic examination of treated cells corresponded with decreased incorporation of $^{125}$IUdR. Inhibition of growth was expressed in terms of the ratio of $^{125}$IUdR incorporated by test cells (e.g., human tumor cells) treated with aliquots of TIF relative to $^{125}$IUdR incorporated by the untreated control cells. The column fractions which yielded the most inhibition of tumor cell $^{125}$IUdR incorporation in monolayer culture also gave the most inhibition of tumor cell growth in soft agar. Conditions where increased cell growth was observed under microscopic examination corresponded with increased incorporation of $^{125}$IUdR. Increased cell growth, expressed as percent stimulation, was the ratio of $^{125}$IUdR incorporated by test cells (e.g., normal human cells) treated with aliquots of TIF relative to $^{125}$IUdR incorporated by the untreated control cells.

Mitogen Assay

Test cells (3T3 2-2) were subcultured ($1.5 \times 10^4$ cells/well) on 96-well tissue culture plates (Nunc 167008) in 100 µl of DMEM supplemented with 10% calf serum and incubated for 24 hr at 37° C. The media were then replaced with Waymouth's medium supplemented with 0.5% calf serum (100 µl/well) and incubated for another 24 hr at 37° C. Aliquots from column fractions to be tested were transferred to sterile 12×75 mm tubes (Falcon 2058) containing 50 µl of 1 M acetic acid and lyophilized. Lyophilized samples were resuspended in 300 µl of serum-free Waymouth's medium containing 2 µCi/ml $^{125}$IUdR and assayed in triplicate. One hundred microliters of resuspended sample were added to each well containing test cells and 100 µl of Waymouth's with 0.5% calf serum. After another 24 hr incubation at 37° C., the monolayers were washed and harvested as described above for the tumor inhibiting factor assay.

MIXING EXPERIMENT

Figure 4:
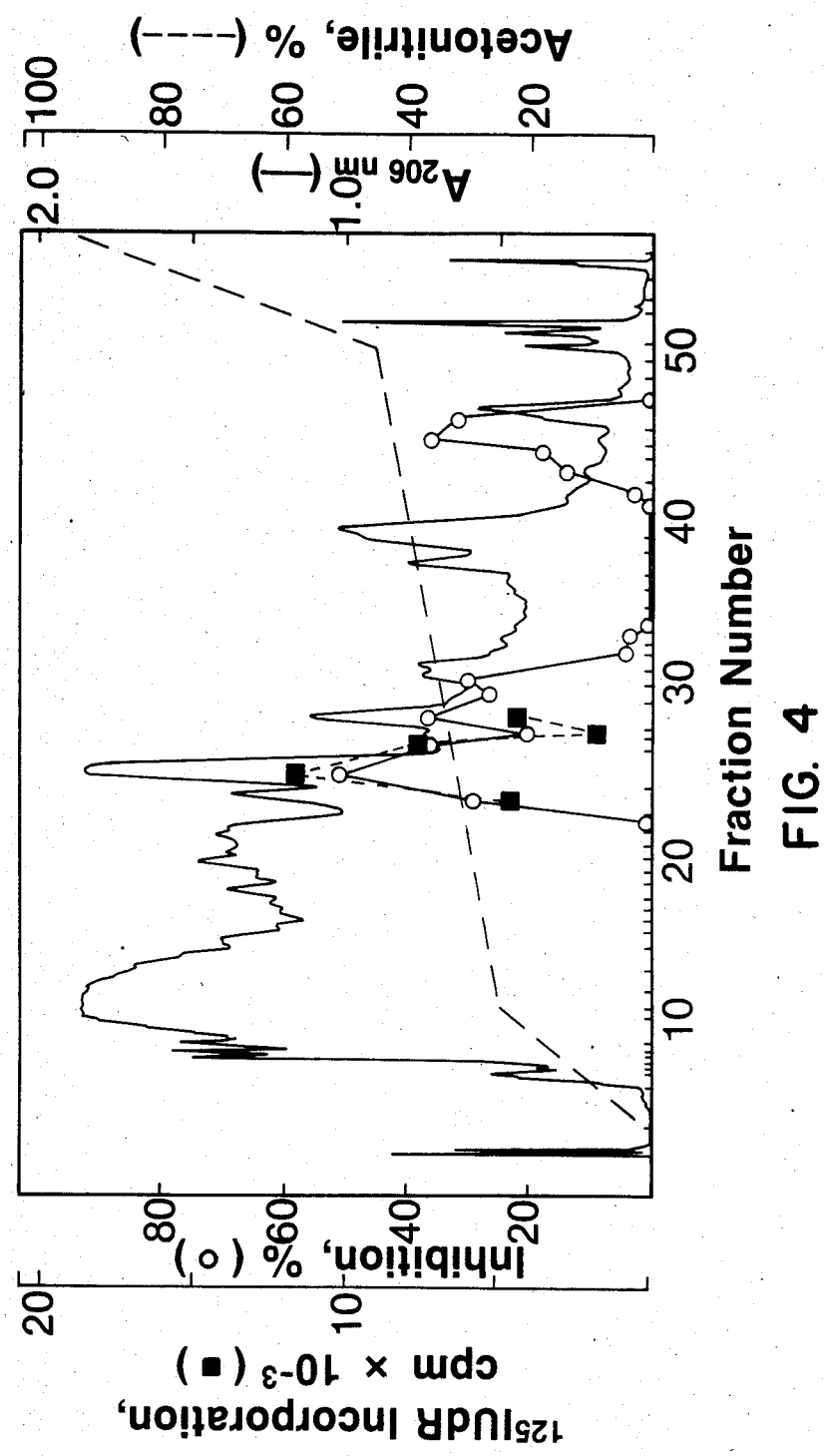
FIG. 4 shows the reverse-phase high performance liquid chromatography (rp-HPLC) of Pool B of FIG. 1.

The combined fractions containing TIF-1 activity eluting between 28–33% acetonitrile from the rp-HPLC purification step in FIG. 4 was used in this experiment. The 20,000 MW TGF derived from Pool A of the Bio-Gel P-100 column (FIG. 1) was purified on rp-HPLC on a µBondapak $C_{18}$ column eluting on a linear gradient at 20% acetonitrile in 0.05% trifluoroacetic acid which was then further purified on a µBondapak $C_{18}$ column eluting on a linear gradient at 12% 2-propanol in 0.05% trifluoracetic acid. A549 cells ($1.5 \times 10^3$ cells per assay) were mixed with TGF and/or TIF-1 in a total volume of 0.3 ml complete medium. A 0.64 ml volume of 0.5% agar was mixed with each fraction and the suspension added to a 0.5% agar base layer in 24 well tissue culture dishes (Nunc 169690). Dishes were incubated at 37° C. in a humidified 5% $CO_2$/95% air atmosphere. Colonies were stained at three weeks by adding 0.5 ml of 0.052% p-iodonitrotetrazolium violet (11). (A) Untreated control; (B-D) cells treated with serial 1:5 dilutions (15 μg/ml protein in B) of TIF-1; (E) 12 ng equivalents/ml TGF (ng equivalents are defined as the concentration of TGF which competes for a known concentration of EGF in a radioreceptor assay); (F-H) cells treated with 12 ng equivalents/ml TGF and with serial 1:5 dilutions (15 μg/ml protein in F) of TIF-1.

Characterization of TIF

Trypsin sensitivity was tested by incubating 76 μg TIF (Bio-Gel P-100 Pool B) in 0.9 ml of 0.1 M ammonium acetate (pH 7.4) with 250 μg trypsin (Sigma, T 8253) for 1 hr at 37° C. The trypsin was inactivated by adding 500 μg of soybean trypsin inhibitor (Sigma, T-9003). As a control, 250 μg of trypsin were incubated with 500 μg of soybean trypsin inhibitor for 20 min at room temperature and then this mixture was incubated with TIF for 1 hr at 37° C. Both treated and control TIFs were incubated for another hour at room temperature followed by the addition of 0.2 ml of 1 M acetic acid to each sample and immediate lyophilization.

The effect of reducing agents was tested by incubating 76 μg TIF (Bio-Gel P-100 Pool B) in 0.9 ml of 0.1 M $NH_4HCO_3$ containing 0.065 M dithiothreitol (DTT) (Schwarz/Mann, No. 90251) for 1 hr at room temperature. The aliquot of TIF treated with DTT and an untreated control aliquot were transferred to Spectrophor-3 dialysis tubing and extensively dialyzed against 1% acetic acid (vol/vol). The dialyzed samples were then lyophilized and tested for TIF activity.

Heat stability of TIF was tested by resuspending 360-μg aliquots of TIF in 1 ml of 1 M acetic acid and by treating one aliquot for 30 min at 56° C. and another in a boiling water bath for 3 min. The heated aliquots and an unheated control were lyophilized and tested for TIF activity.

EXAMPLE—1

The serum-free conditioned media containing both TGFs and TIFs, derived from the human tumor cell line A673, were fractionated over a Bio-Gel P-100 column (FIG. 1). The majority of protein elutes in the void volume. As can be seen from FIG. 1, there is a sharply defined region of TGF activity in fractions 55-68 which has been designated Pool A ($M_r = 20,000$). TGF activity was determined by the ability of an aliquot from a fraction to compete for binding to receptors for epidermal growth factor (EGF) in a radioreceptor assay as described by Todaro, et al (1980) Proc. Natl. Acad. Sci. USA 77, 5258-5262, which is incorporated herein by reference.

FIG. 1 shows three major regions of TIF activity. Large molecular weight TIF eluted with a $M_r$ 28,000. TIF activity, designated Pool B, (fractions 69-95) corresponds to a $M_r$ of 10-16,000. TIF activity, designated Pool C, (fractions 96-133) corresponds to a $M_r$ of 5-10,000. Each major region of TIF activity has some heterogeneity. None of the 3 regions of TIF activity observed in FIG. 1 contained any TGF activity.

Figure 2:
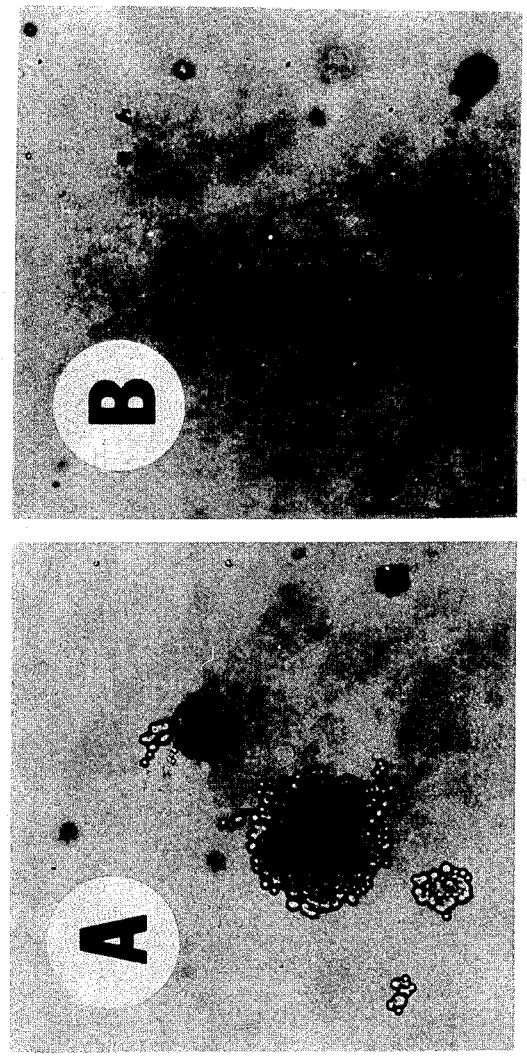
FIG. 2 shows the effect of TIF on soft agar growth of human tumor cells.

Anchorage-independent growth of cells in soft agar is one of the characteristics of tumor cells. Aliquots from each of the regions of TIF activity from the Bio-Gel P-100 column were tested for their effect on human tumor cell growth in soft agar. FIG. 2 is a photomicrograph of human carcinoma A549 cells in soft agar. The untreated control suspension of tumor cells grows in soft agar and forms large colonies. Cells treated with TIF from Pool B are significantly inhibited in its ability to grow in soft agar. As can be seen in the photomicrograph (FIG. 2) treated tumor cells are unable to proliferate in soft agar, but appear not to have undergone cell death and subsequent autolysis. Identical inhibition of A549 growth in soft agar was observed with HPLC purified TIF from Pool B. These results indicate that TIF is growth inhibiting rather than cytotoxic.

The tumor inhibiting activity obtained from serum-free conditioned media is not due to the presence of interferon-like activity. Inhibition of growth of human lung carcinoma cells was observed after treatment with as little as 3 International Units (IU) of interferon. A comparable inhibition of tumor cell growth was observed with 360 ng/ml of TIF from Pool B (FIG. 1) and no interferon activity is detected when a 1000-fold concentration of this TIF sample was tested.

When normal human fibroblasts (HuF) and a human lung carcinoma (A549) were treated with increasing concentrations of TIF-1, there was a concentration-dependent inhibition of the human tumor cells, but a concentration-dependent stimulation of normal human fibroblasts. Human tumor cells were inhibited by TIF-1, whereas normal human fibroblasts were not. TIF-1, therefore, does not inhibit the growth of all cells.

Figure 3:
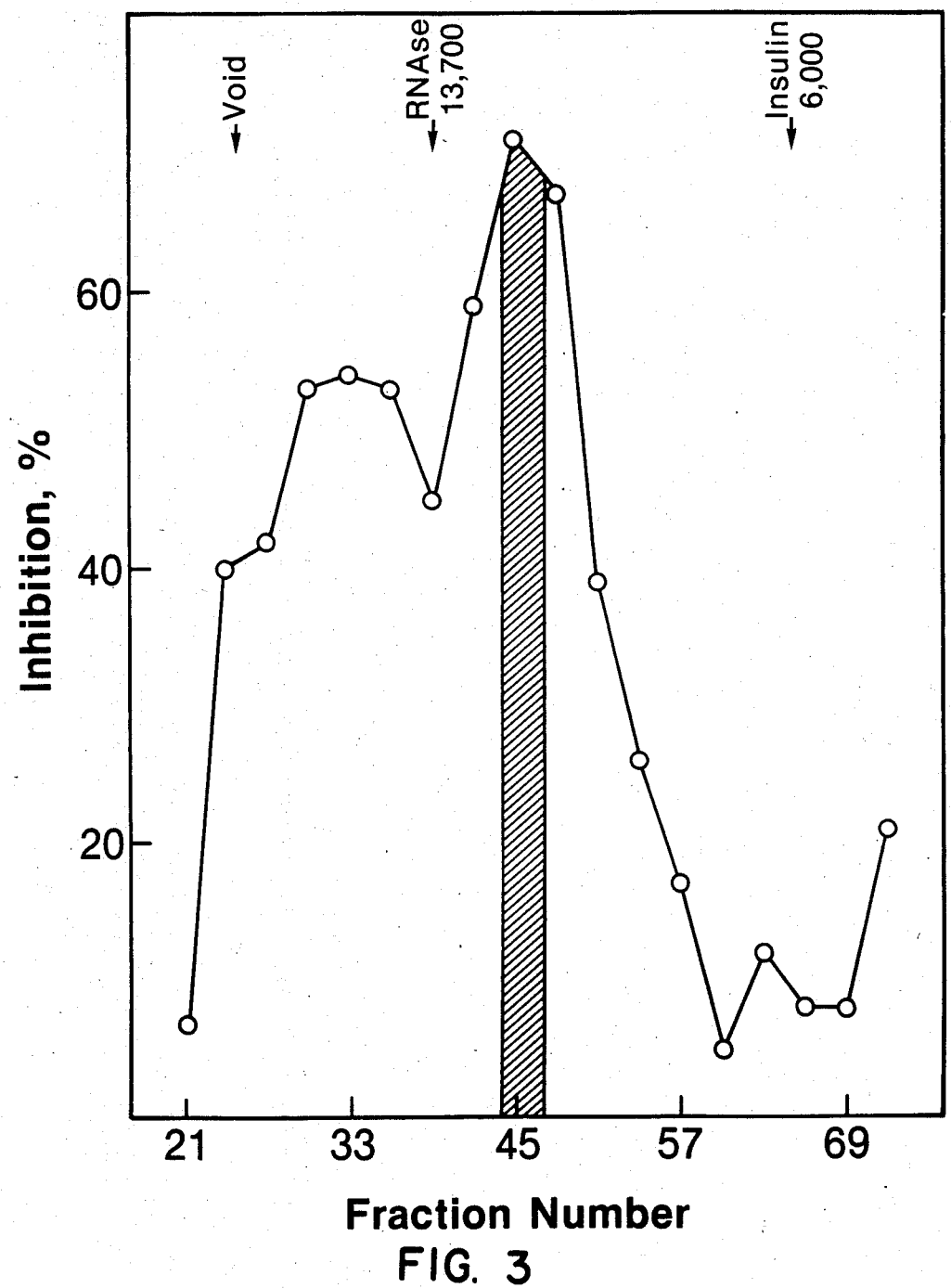
FIG. 3 shows the elution pattern on Bio-Gel P-10 chromatography of Pool B of FIG. 1.

TIF-1 was purified from Pool B (FIG. 1) by rp-HPLC using a μBondapak $C_{18}$ column using three linear step-gradients with acetonitrile/0.05% TFA as shown in FIG. 4. Elution was achieved with a linear 15-min gradient of 0-25% acetonitrile in 0.05% trifluoroacetic acid, followed by a linear 80-min gradient of 25-45% acetonitrile in 0.05% trifluoroacetic acid, followed by a linear 15-min gradient of 45-100% acetonitrile in 0.05% trifluoroacetic acid. TIF activity is observed to elute at two distinct acetonitrile concentrations: between 28% and 33% acetonitrile and between 38% and 42% acetonitrile. All preparations of TIF-1 derived from Pool B (FIG. 1) had two peaks of TIF activity which eluted between 28% and 33% acetonitrile on rp-HPLC. These TIF activities were designated TIF-1. The TIF activity eluting between 38% and 42% acetonitrile was occasionally observed when some overlapping fractions from Pool A, were combined in Pool B (FIG. 1) and purified by rp-HPLC (FIG. 4). Combined fractions from the shaded portion of the Bio-Gel P-10 column (FIG. 3) yielded only the two peaks of TIF-1 activity which elute between 28% and 33% acetonitrile on rp-HPLC.

It was observed that TIF-1 inhibited the growth of human lung carcinoma cells, while the growth of normal human fibroblasts was stimulated. TIF-1 was, therefore, tested for mitogenic activity on serum-starved quiescent 3T3 mouse cells. The amount of TIF activity in aliquots from fractions containing TIF-1 coincided with the amount of mitogenic activity observed (FIG. 4). This coincidence of TIF inhibitory activity on human tumor cells with mitogenic activity on normal mouse as well as normal human cells was observed in all stages of TIF purification. TIF-1 may, therefore, have different biological properties depending upon the nature of the target cells.

Figure 5:
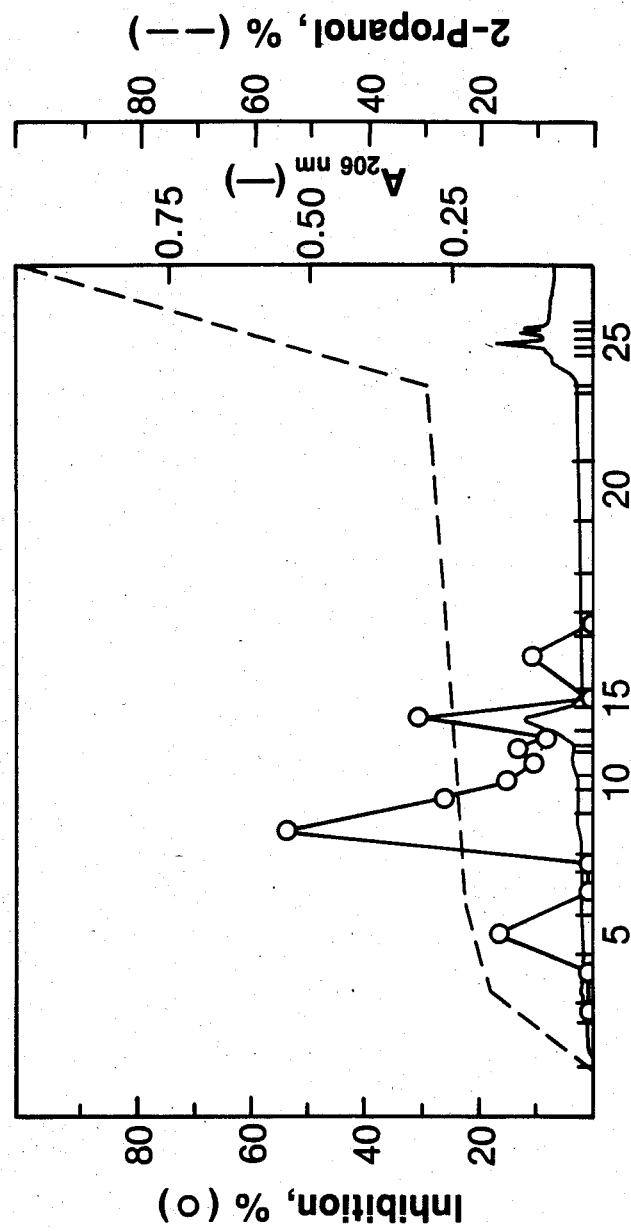
FIG. 5 shows purification of TIF-1 on a μBondapak $C_{18}$ column (0.39×30 cm) eluted with 2-propanol.

TIF-1 activity eluting between 28% and 33% acetonitrile on a μBondapak $C_{18}$ column (FIG. 4) was further purified on rp-HPLC using a μBondapak $C_{18}$ column with a linear 2-propanol gradient (FIG. 5). Elution was achieved with a linear 10-min gradient of 0.18% 2-propanol in 0.05% trifluoroacetic acid, followed by a linear 10-min gradient of 18–22% 2-propanol in 0.05% trifluoroacetic acid, followed by a linear 60-min gradient of 22–28% 2-propanol in 0.05% trifluoroacetic, followed by a linear 10-min gradient of 28–30% 2-propanol in 0.05% trifluoroacetic acid, followed by a linear 15-min gradient of 30–100% 2-propanol in 0.05% trifluoroacetic acid. TIF-1 was observed to elute between 18% and 22% 2-propanol. TIF-1 purified on rp-HPLC with a linear gradient of 2-propanol yielded significant TIF activity at concentrations of ng/ml as approximated by absorbance at 206 nm.

PROPERTIES OF TIF-1

Some of the characteristics of TIF-1 are summarized in Table 1. TIF-1 is inactivated by trypsin and DTT. This suggests that TIF-1 is a protein which requires intact disulfide linkages for activity. TIF-1 is heat-stable at 56° C. for 30 min and 100° C. for 3 min. Inhibition of the growth of human carcinoma cells was 95% reversible if TIF-1 was removed within 1 hr. Longer exposure of tumor cells to TIF-1 resulted in a corresponding increase in inhibition of growth.

TABLE 1

| Characteristics of TIF | | |
|---|---|---|
| TIF-1 μg/ml | Treatment | % Inhibition of A549 |
| 76 μg | Control | 51 |
| 76 μg | Trypsin | 12 |
| 76 μg | Control | 57 |
| 76 μg | DTT | 16 |
| 360 μg | Control | 63 |
| 360 μg | 56° 30′ | 62 |
| 360 μg | 100° 3′ | 55 |

The spectrum of inhibitory activity of TIF-1 on the growth of different human and nonhuman cell lines is shown in Table 2. It should be noted that the growth of normal human cells was stimulated by TIF-1. These studies included a normal human fibroblast strain which was maintained for 10–25 passages in vitro; a very early passage of a human fibroblast (6 passages from tissue explant); and a very low passage (3 passages from explant) of a normal human epithelial cell. The growth of all human tumor cells tested was inhibited to some degree by TIF-1. Some cells, such as the lung adenocarcinoma A549 and the breast carcinoma MCF 7, were very sensitive to inhibition of growth by TIF-1. Other tumor cells, such as the bladder cancer and the melanoma, were less sensitive to growth inhibition. Normal mink lung epithelial cells were also very sensitive to growth inhibition by TIF-1.

TABLE 2

| | Effect of TIF on different cell lines | | |
|---|---|---|---|
| | TIF-1 | $^{125}$IUdR incorporation | |
| Cell line | Concentration μg/ml | Percent inhibition | Percent stimulation |
| Normal human | | | |
| HuF foreskin fibroblast | 46 | 0 | 103 |
| TOD adult skin fibroblast | 36 | 0 | 111 |
| HEK p3 embryonic kidney | 360 | 0 | 20 |
| Human tumors | | | |
| A549 p17 adenocarcinoma of lung | 58 | 68 | 0 |
| A549 p38 | 58 | 33 | 0 |
| A673 p10 rhabdomyosarcoma | 349 | 59 | 0 |
| A673 >p70 | 349 | 10 | 0 |
| A2058 p13 melanoma | 46 | 62 | 0 |
| MCF-7 breast cancer | 46 | 57 | 0 |
| A1723 p13 glioblastoma | 360 | 44 | 0 |
| HTB-48 p39 kidney cancer (Wilm's) | 180 | 33 | 0 |
| A427 p180 lung carcinoma | 180 | 12 | 0 |
| A375 Ag5 melanoma | 23 | 18 | 0 |
| A1163 p26 bladder cancer | 58 | 8 | 0 |
| Nonhuman | | | |
| CCL 64 normal mink lung | 8 | 84 | 0 |
| CCL 46 (P388D$_1$) mouse lymphoid neoplasm | 46 | 40 | 0 |

The effect of maintenance of human tumor cells in tissue culture on sensitivity to inhibition of growth by treatment with TIF-1 was also examined. The longer a human tumor cell is maintained in tissue culture, the more resistant to growth inhibition it became when treated with TIF-1. Both the human rhabdomyosarcoma (A673), which was the tumor cell source of TIF-1, and lung carcinoma (A549) show this effect (Table 2). Low passage cells are very sensitive to growth inhibition but, with a higher number of passages in tissue culture, the tumor cells become more resistant. It is believed that the closer the human tumor is to the primary explant, the more responsive it is to inhibition by TIF-1.

The growth of all of the human tumor cells listed in Table 2 was inhibited by treatment with TIF-1. The effect of TIF-1 on virally transformed cells is shown in Table 3. As was observed in Table 2, the growth of the normal human fibroblast Wi38 was not inhibited by treatment with TIF-1, rather a stimulation of growth is observed. The growth of the SV40 transformed counterpart Wi38 cells (75.1), however, was significantly inhibited by TIF-1. This inhibition of virally transformed cells was also observed with rat cells. The growth of normal rat kidney cells (NRK) was not inhibited by TIF-1. However, a slight stimulation of growth of these cells treated with TIF-1 was observed. Kirsten sarcoma virus-transformed NRK(KNRK) cell growth was also inhibited by TIF-1. The growth of cells transformed with DNA and RNA viruses is inhibited by TIF-1 whereas the growth of the parent, untransformed cells is stimulated.

TABLE 3

| Cell line | TIF-1 concentration μg/ml | $^{125}$IUdR incorporation Percent inhibition | $^{125}$IUdR incorporation Percent stimulation |
|---|---|---|---|
| Wi-38 human embryonic lung (CCL 75) | 325 | 0 | 18 |
| Wi-38 SV$_{40}$ transformed (CCL 75.1) | 325 | 30 | 0 |
| NRK-49F normal rat kidney (CRL 1570) | 58 | 0 | 18 |
| KNRK Kirsten transformed NRK (CRL 1569) | 58 | 45 | 0 |

Figure 6:
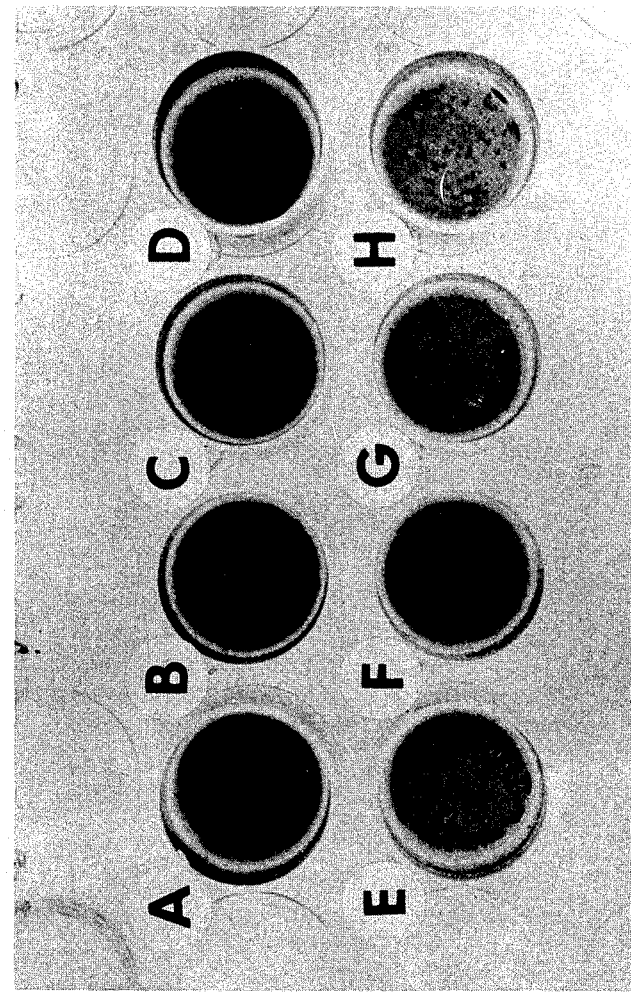
FIG. 6 shows antagonistic relationship between TIF-1 and TGF derived from the same conditioned medium.

Conditioned media from human tumor cells was observed to contain both tumor growth factors (TGFs) and inhibitors of tumor cell growth (TIFs). The effect of TIF, TGF (both derived from the same source of tumor cell conditioned media), and mixtures of TIF and TGF on the growth of human lung carcinoma cells (A549) in soft agar is shown in FIG. 6 (see Mixing Experiment, supra). Well A is the untreated control suspension of A549 cells which form colonies in soft agar. Wells B-D contain a soft agar suspension of cells treated with various dilutions of TIF-1. Well B was treated with 15 μg/ml of TIF-1. There is significant inhibition of the tumor cell growth in soft agar. Wells C and D were treated with 3.0 and 0.6 μg/ml of TIF-1 respectively, and show less inhibition of soft agar growth of tumor cells as the TIF concentration is decreased. However, there is still visible inhibition of tumor cell growth in the soft agar suspension of A549 cells treated with 0.6 μg/ml of TIF-1. The lower row, wells E-H, shows the effect of TGF (derived from the same conditioned media that yielded the TIF used in wells B-D) on soft agar growth of A549 cells. Well E was treated with 12 ng equivalents/ml of TGF. The 20,000 $M_r$ TGF enhances the growth of the human carcinoma cells in soft agar. Well F was treated with both TGF (12 ng equivalents/ml) and TIF-1 (15 μg/ml). The soft agar growth of human tumor cells is significantly inhibited by TIF-1, even in the presence of TGF at concentrations that enhanced soft agar growth of tumor cells in Well E. In wells F-H, decreasing TIF concentrations resulted in increased growth of TGF treated tumor cells in soft agar. The colony size of human tumor cells in soft agar with different treatments is shown in Table 4. Untreated human carcinoma cells form soft agar colonies 0.3 mm in diameter. Human carcinoma cells treated with 12 ng equivalents/ml of TGF form larger soft agar colonies 0.5 mm in diameter. Tumor cells treated with TIF form smaller soft agar colonies with size dependent upon TIF concentration. Tumor cells treated with a mixture of 12 ng equivalents/ml of TGF and 3 μg/ml TIF-1 form soft agar colonies with the same size as control tumor cells which have not been treated by either TGF or TIF.

TABLE 4

Quantitation of the Antagonistic Relationship Between TIF and TGF Derived From the Same Conditioned Medium

| | Untreated | With TGF 12 μg/ml EGF Equivalents |
|---|---|---|
| Control | 0.31 ± 0.04 mm | 0.52 ± 0.12 mm |
| Tumor Inhibiting Factor Added | | |
| 15 μg/ml | 0.08 ± 0.02 mm | 0.18 ± 0.13 mm |
| 3 μg/ml | 0.14 ± 0.05 mm | 0.37 ± 0.06 mm |
| 0.6 μg/ml | 0.28 ± 0.11 mm | 0.62 ± 0.04 mm |
| 0.12 μg/ml | 0.22 ± 0.05 mm | 0.52 ± 0.07 mm |
| 0.024 μg/ml | 0.30 ± 0.06 mm | 0.61 ± 0.21 mm |

It is concluded from these results that TIF inhibits anchorage-independent growth of tumor cells in soft agar, (2) TGF enhances anchorage-independent growth of tumor cells in soft agar, (3) Although TIF-1 does not compete for binding to EGF receptors, it is antagonistic to the effect of TGFs on anchorage-independent growth of tumor cells in soft agar. When EGF was substituted for TGF in a similar mixing experiment, identical results were observed.

The results from the mixing experiment (Table 4) show that TGF can neutralize the effect of TIF-1 in an in vitro soft agar assay. In FIG. 1, TIF activity was not detected in Pool A, which contained the TGF activity When Pool A containing the 18-20,000 $M_r$ TGF was purified on rp-HPLC, TIF activity was separated from TGF and observed to elute between 38-42% acetonitrile The TGF in Pool A was apparently masking the presence of the 18-20,000 $M_r$ TIF.

As was shown in a Table 2, TIF stimulates the growth of normal cells. Therefore, the possibility that TIF may be mitogenic and able to stimulate DNA synthesis in quiescent cells, such as serum-starved mouse cells, by interacting with the EGF receptor was investigated. It was found that both EGF and TIF-1 possessed substantial mitogenic stimulation of a mouse cell line NIH clone 7. The same experiment using NR6/6 cells, a mouse cell line with no functional EGF receptors, showed that EGF has no mitogenic activity, but that TIF-1 does act as a mitogen. The growth stimulatory and mitogenic activities, therefore, are not believed to function through the EGF receptor.

In summary, it can be seen from the above that several tumor inhibiting factors (TIFs) are produced by a human tumor cell line, A673, with molecular weights of 28,000, 18-22,000, 10-16,000, and 5-10,000 being observed from Bio-Gel P-100 gel permeation chromatography. A 10-16,000 $M_r$ TIF, designated TIF-1, was partially purified and characterized. TIF-1 was found to be acid- and heat-stable protein which was inactivated by treatment with trypsin and DTT. It inhibited the growth of a wide range of human tumor cells to a varying degree, virally transformed human and rat cells, as well as normal mink lung epithelial cells. TIF-1 did not inhibit the growth of any of the normal human fibroblasts or epithelial cells tested. In fact TIF-1 stimulated the growth of normal human fibroblast and epithelial cells.

The mixing experiment (FIG. 6 and Table 4) shows how tumor cells can produce both tumor inhibiting factors (TIFs) and (TGFs) and still express the tumorogenic phenotype. Tumor cells that produce more TIF than TGF may become benign or regress, whereas those that are more aggressive and that metastisize may produce more TGF than TIF. The inappropriate production of TGFs and TIFs may be a consequence of tumorigenesis. The ratio of TIF to TGF production, therefore, could serve as an important determinant of the extent of tumor cell proliferation. The exogenous addition of TIF can be a very potent means to control tumor cell proliferation without affecting normal cells.

PREPARATION OF TIF-2

Cell Cultures

Cell cultures were maintained at 37° C. in 75 cm$^2$ tissue culture flasks (Falcon, 3024)with Dulbecco's modification of Eagle's medium (DMEM) with 10% FBS (Gibco) as described herein supra.

Source of TIF's and TGF

Serum-free conditioned media from the human rhabdomyosarcoma line, A673, was processed and chromatographed by Bio-Gel P-100 in 1 M HOAC as has been described herein supra.

Chromatography on CM-cellulose

TGF active fractions obtained by the procedure described herein supra, from several Bio-Gel P-100 columns were pooled, lyophilized, and reconstituted in 5 ml of 1 M HOAC and dialyzed against 5 mM NH$_4$OAc (pH 4.5) overnight at 4° C. The sample was centrifuged at 175,000×g for 30 min at 22° C. and applied to a 1.5×3 cm cation exchange column of carboxymethylcellulose (Whatman, CM-23). Elution was achieved with a linear gradient pumped from a two-chamber, constant-level device containing 200 ml of starting buffer (5 mM NH$_4$OAc, pH 4.5) in the first chamber and 200 ml of limit buffer (0.5 M NH$_4$OAc, pH 6.8) in the second (flow rate 80 ml/hr at 22° C.) Fraction aliquots were sterilized by adding 0.5 ml of 1 M HOAc and lyophilized before testing.

Reverse-Phase High-Pressure Liquid Chromatography (rp-HPLC)

A TIF-2 biologically active region from a CM-cellulose column was pooled, lyophilized, and resuspended in 1 ml of 0.05% trifluoroacetic acid and centrifuged for 5 min at 1000×g to remove insoluble material before injection. The supernatant was injected on a Water's μBondapak C$_{18}$ column (0.39×30 cm). Water's gradient liquid chromatography equipment was utilized and the column eluate was monitored with a variable wavelength u.v. detector set at 214 nm. Aliquots from each fraction were lyophilized before testing.

Soft Agar Assay

A suspension of 1×10$^4$ A375 Ag 5 cells was mixed with lyophilized TIF-2 and 0.34% agar (Difco, Noble) in a total volume of 0.94 ml DMEM with 10% FBS. It was immediately pipetted over a base layer of 0.5% agar in a 35 mm tissue culture dish (Falcon,3001). Cells were incubated at 37° C. in a 5% CO$_2$/95% air humidified atmosphere and photomicrographs were made at 8 days.

Tumor Inhibiting Factor Assay

Test cells were subcultured, treated with TIF-2, and tested for $^{125}$IUdR incorporation as has been described herein supra. Inhibition is expressed as percent of control, stimulation as percent above control.

Mitogenic Activity Assay

NIH clone 7 and HuF cells were subcultured in DMEM with 10% FBS at a density of 1×10$^4$ cells per well in 96-well tissue culture plates (Nunc 167008). After 24 hours incubation at 37° C., they were serum-starved for 72 hours by replacing media with Waymouth's media containing 0.1% FBS (100 μl/well). Cells were treated with TIF-2 and tested for $^{125}$IUdR incorporation as described herein supra.

TGF Assay

TGF activity was determined by ability to compete in a $^{125}$I-EGF radioreceptor binding assay as described herein supra.

EXAMPLE—2

Figure 7:
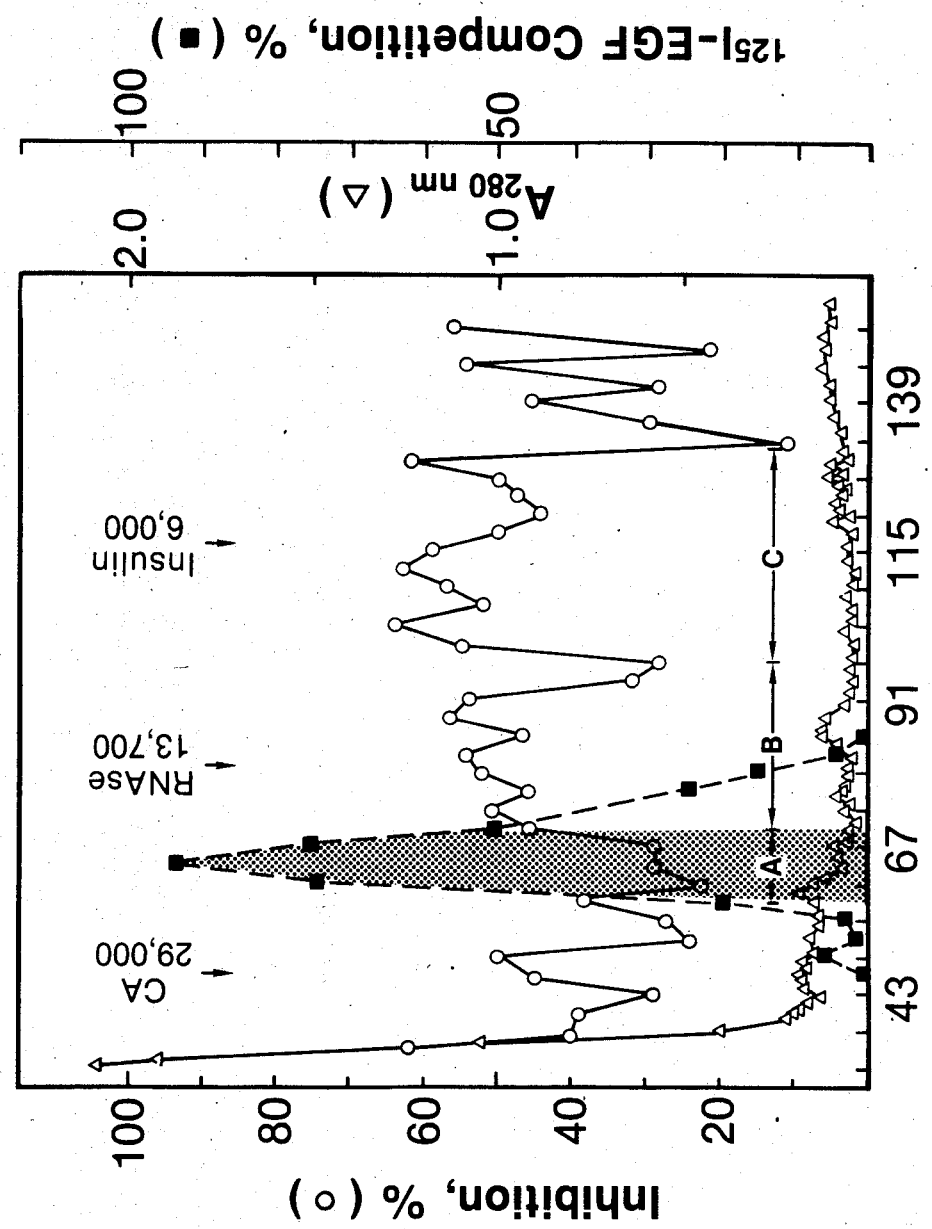
FIG. 7 shows biological activity and protein determination of Bio-Gel P-100 column fractions of conditioned media from a human rhabdomyosarcoma cell line, A673.

Thirty liters of serum-free conditioned media from A673 cells were concentrated, lyophilized, and 280 mg of protein extracted with 1 M acetic acid. This was applied to a Bio-Gel P-100 column packed in 1 M acetic acid. Aliquots of every third fraction were tested for TGF and TIF activity. Major peaks of tumor inhibitory activity were found in the 10,000–16,000 molecular weight region (B pool) and 5,000–10,000 molecular weight region (C pool) as shown in FIG. 7. In the 18,000–22,000 molecular weight region (A pool) much less inhibitory activity was observed but it contained major TGF activity.

Figure 8:
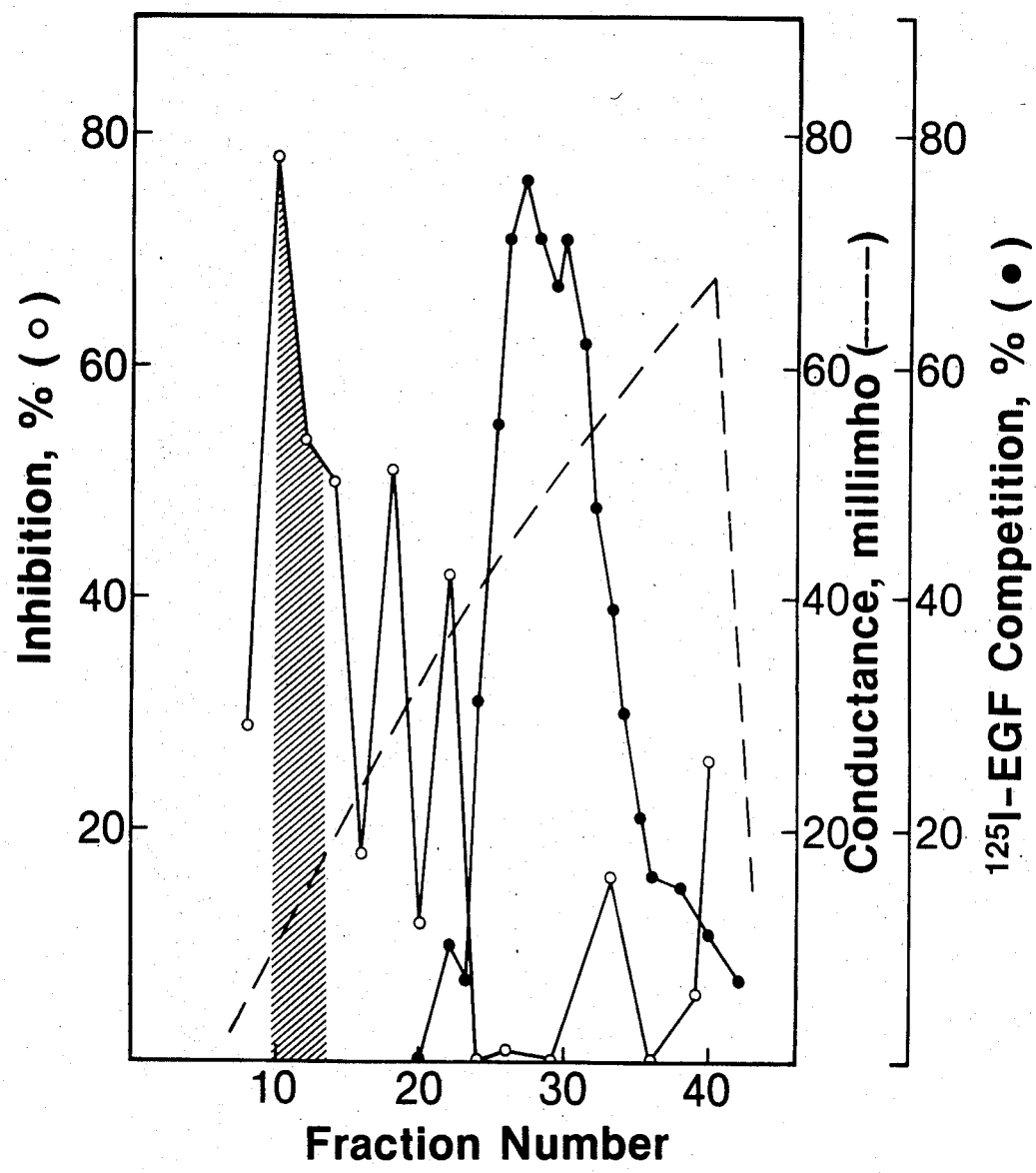
FIG. 8 shows CM-cellulose chromatography of TGF active pools from several Bio-Gel P-100 columns as in shaded area of FIG. 7 (Pool A).
Figure 9:
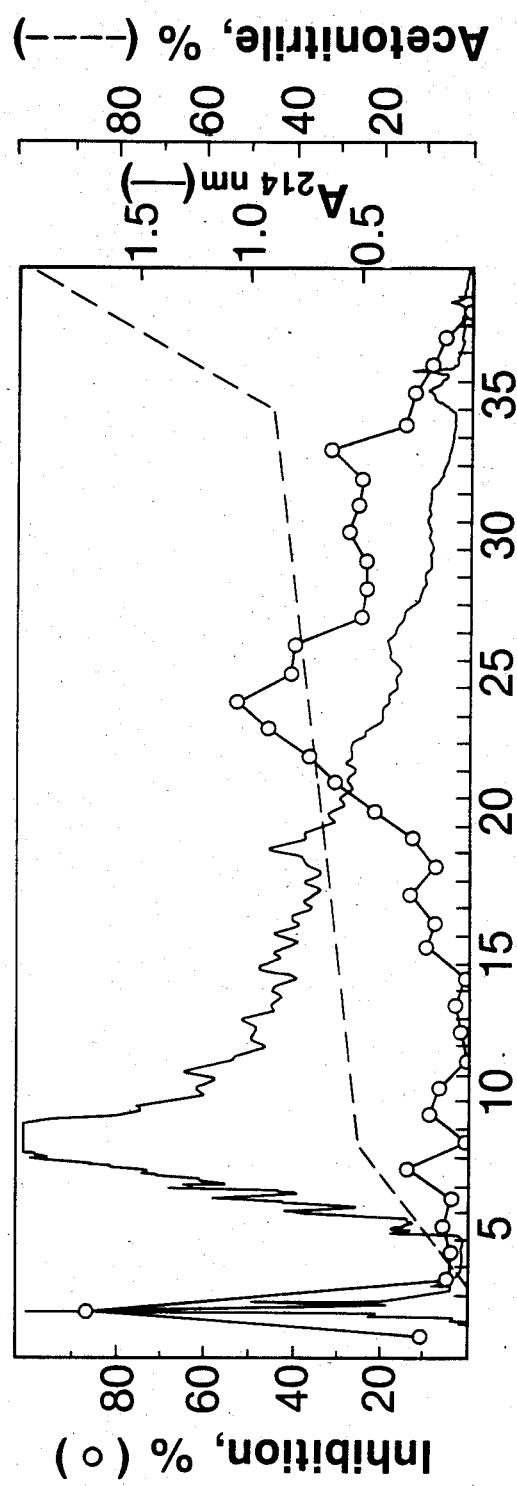
FIG. 9 shows RP-HPLC of CM-cellulose purified TIF-2.

The TGF fractions (A pool) from several Bio-Gel P-100 colums were further purified by CM-cellulose chromatography. This material originally came from 227 liters of conditioned media. Total protein applied to the CM-cellulose column (FIG. 8) in these combined pools was 85 mg. Aliquots of every other fraction were tested for TGF activity and TIF activity. This column profile suggests that probably the TGF was masking the TIF activity because a large peak of inhibitory activity could be separated away from the TGF. The shaded area representing the peak tumor inhibitory activity was pooled, lyophilized, and rechromatographed on a reverse phase Water's μBondapak C$_{18}$ column with a linear acetonitrile gradient. Elution was achieved with a linear 15-min gradient of 0–25% acetonitrile in 0.05% trifluoroacetic acid, followed by a linear 80-min gradient of 25–45% acetonitrile in 0.05% trifluoroacetic acid, followed by a linear 15-min gradient of 45–100% acetonitrile in 0.05% trifluoroacetic acid. This is shown in FIG. 9. Each fraction was lyophilized and tested for TIF activity. The major peak of TIF activity elutes between 38–42% acetonitrile. TIF-1 has previously been shown to elute between 28–33% acetonitrile. TIF-2 can be further purified on HPLC using a linear 2-propanol gradient. TIF-1 has been shown to elute between 19–21% 2-propanol, whereas TIF-2 elutes between 29–31% 2-propanol.

PROPERTIES OF TIF-2

Figure 10:
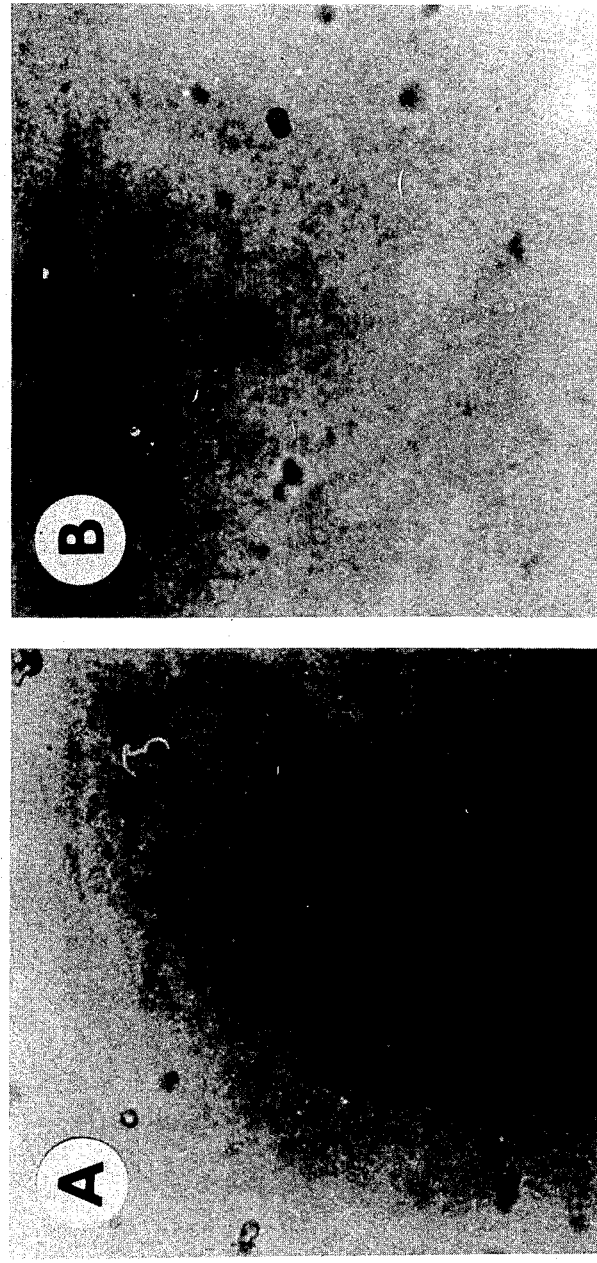
FIG. 10 shows effect of TIF-2 on the growth of human melanoma cells, A375 Ag 5, in soft agar.

A375 Ag 5 cells were treated with TIF-2 (64 μg/ml) and photomicrographs made at eight days. As shown in FIG. 10, untreated cells typically grow to colony sizes averaging 0.5 to 1 mm in diameter comprised of approximately 100–200 cells. When these cells were treated with CM-cellulose purified TIF-2, colony size was significantly reduced. The small colony growth that is seen occurred in the first few days after treatment and typically no recovery of growth is observed after even three weeks. The cells are alive and therefore TIF-2 is not cytotoxic.

The level of purification from CM-cellulose chromatography to HPLC was 125 fold as shown in Table 5. Material from each purification step was tested in the tumor inhibitory assay. $^{125}$IUdR incorporation was determined for both A549 cells and the normal human fibroblast line, HuF. In both preparations, inhibition of A549 cells and a stimulation of HuF cells was seen. Since TIF-1 stimulates growth of normal fibroblasts and also acts as a mitogen, TIF-2 was tested in a mitogen assay using normal mouse cells (NIH clone 7) and HuF cells. The assay was performed on serum-starved cells with the addition of factors to be tested and $^{125}$IUdR added at the same time for 24 hours. TIF-2 at 54 μg/ml increased the level of $^{125}$IUdR incorporation considerably more than did 10% FBS. The same concentration on human fibroblasts gave comparable levels of incorporation as 10% FBS. It was found that TIF-2 is a potent mitogen even at concentrations as low as 500 ng per ml in mouse NIH clone 7 cells. On the other hand mitogenic activity with TIF-1 can be induced with a concentration as low as 20 ng/ml.

TABLE 5

Comparison of CM-cellulose and HPLC purified TIF-2 from A673 conditioned media

| | | $^{125}$IUdR incorporation | | | |
|---|---|---|---|---|---|
| | | A549 p23 | | HuF | |
| Purification | Amount μg/ml | Percent inhibition | Percent stimulation | Percent inhibition | Percent stimulation |
| CM-cellu- | 3250 | 57 | 0 | 0 | 27 |
| lose | 325 | 37 | 0 | 0 | 38 |
| HPLC | 26 | 63 | 0 | 0 | 80 |
| | 2.6 | 40 | 0 | 0 | 37 |

TIF-2 was tested for interferon activity in an antiviral interferon assay conducted by Meloy Laboratories, Inc., Springfield, Va. and some of their leukocyte interferon (PIF Lot P-321) was tested in our tumor inhibitory assay using A549 cells. Leukocyte interferon could be detected at 3 IU/ml in the TIF assay (25% inhibition). A 100-fold concentration of TIF-2 which gave comparable inhibition as 3 IU/ml of interferon, was tested in the antiviral assay and the results were negative. This indicates that TIF-2 has no antiviral activity and is therefore not an interferon.

HPLC purified TIF-2 (39 μg/ml) was tested for trypsin sensitivity as described for TIF-1. It was not trypsin sensitive. An aliquot of TIF-2 (13 μg/ml, HPLC purified) was heated for 30 min at 56° C., another for 3 min at 100° C., and a control kept at room temperature. Each was lyophilized and tested in the tumor inhibitory assay with A549 as the test cell. Activity was stable at 56° C. but less stable at 100° C. with inhibition dropping from 53% to 35%.

TIF-2 was tested on a variety of normal and tumor cells for its effect on $^{125}$IUdR incorporation (Table 6). All human fibroblasts tested were stimulated. In addition, a low passage human embryonic kidney cell line was also stimulated. Only epithelial cells could be seen in this culture. In contrast to this, all human tumor lines tested showed some inhibition though sensitivity to inhibition varied. The number of passages in tissue culture may contribute to some of the variations as can be seen by looking at the differences in inhibition seen with early and late passages of A549 and A673. The closer the tumor is to the primary culture, the more sensitive to inhibition by TIF-2. The breast cancer line, MCF-7 and A549, which is the usual test cell, were observed to be the most sensitive to TIF-2. It has been shown that the normal mink lung cell line is most responsive to inhibition by TIF-1. In contrast, TIF-2 has little or no effect on mink cells.

TABLE 6

Effect of TIF-2 on different cell lines

| | TIF | $^{125}$IUdR incorporation | |
|---|---|---|---|
| Cell line | concentration μg/ml | Percent inhibition | Percent stimulation |
| Normal human | | | |
| HuF foreskin fibroblast | 325 | 0 | 79 |
| TOD adult skin fibroblast | 325 | 0 | 60 |
| HEK p3 embryonic kidney | 325 | 0 | 21 |
| Human tumor | | | |
| A549 p17 adenocarcinoma of lung | 325 | 46 | 0 |
| A549 p38 | 325 | 0 | 3 |
| A673 p10 rhabbdomyosarcoma | 325 | 53 | 0 |
| A673 > p70 | 325 | 19 | 0 |
| MCF-7 breast cancer | 130 | 63 | 0 |
| A2058 p13 melanoma | 650 | 55 | 0 |
| A1663 p26 bladder cancer | 325 | 14 | 0 |
| A1723 p15 glioblastoma | 325 | 24 | 0 |
| HTB-48 p39 kidney cancer (Wilm's) | 244 | 33 | 0 |
| HTB-52 p22 liver cancer | 244 | 20 | 0 |
| T24 bladder cancer | 244 | 7 | 0 |
| A427 p180 lung carcinoma | 244 | 9 | 0 |
| Nonhuman | | | |
| CCL 64 normal mink lung | 325 | 5 | 0 |
| SV 3T3 clone 5 SV40 transformed mouse cells | 325 | 36 | 0 |
| CCL 46 (p388D$_1$) mouse lymphoid neoplasm | 325 | 38 | 0 |

The effect of SV40 virus transformation on the sensitivity to TIF-2 was examined. The human embryonic lung cell Wi-38 (CCL 75) and its SV40 transformed counterpart (CCL, 75.1) were both tested for $^{125}$IUdR incorporation after TIF-2 treatment. Wi-38 cells were stimulated (11%) and the Wi-38 SV40 transformed cells were inhibited (24%). The same effect is seen with TIF-1 and emphasizes that the transformed phenotype may be necessary for inhibition by TIFs.

A comparison was made of inhibitors and interferon on the human melanoma clonal line A375 Ag 5 and a TIF-1 resistant variant line of A375 Ag 5, designated A375 Ag 5-IR (Table 7). To derive this line A375 Ag 5 cells (1×10$^4$) were treated in monolayers on 24-well plates (Nunc 169590) with an active fraction of TIF-1 taken from a Bio-Gel P-100 column run on A673 conditioned media. Cells were treated once but factor remained on the cells for 10 days. Treated cells became enlarged, more rounded and no longer attached to the plate. These treated cells were transferred to a Falcon tissue culture flask (3013). Cells eventually settled and grew as a monolayer. After several passages in monolayers, this line grew as fast as the parent line, A375 Ag 5. When both cell lines were plated in soft agar A375 Ag 5 was observed to grow in soft agar with colonies averaging 0.5–1.0 mm in diameter. In contrast, the A375 Ag 5-IR variant showed almost no soft agar growth with a few small 3–5 cell colonies. Both of these lines were tested in a tumor unhibitory assay. As shown in Table 7, the parent line A375 Ag 5 can be inhibited by TIF-1, TIF-2, and partially purified intereferon. The varient A375 AG 5-IR is still just as sensitive to ihibition by TIF-2 and interferon but has lost its sensitivity to TIF-1. This gives further evidence that there are two classes of inhibitors and that different cells may respond in different ways.

TABLE 7

Comparison of tumor inhibitors on A375 Ag5 and TIF-1 resistant A375 Ag5-IR.

| Sample | Amount μg/ml | $^{125}$IUdR incorporation | |
|---|---|---|---|
| | | Percent inhibition of A375 Ag5 | Percent inhibition of A375 Ag5-IR |
| TIF-1 | 173 | 54 | 20 |
| | 17.3 | 44 | 2 |
| TIF-2 | 975 | 97 | 93 |
| | 97.5 | 34 | 25 |
| Interferon (partially purified) | 1000 IU/ml | 55 | 54 |

Further distinction between TIF-1 and TIF-2 as to their inhibitory activity is shown by the data in Table 8.

TABLE 8

Comparison of Inhibitory Activity of TIF-1 and TIF-2 on Human Lung Carcinoma Cells and Normal Mink Lung Cells.

| | TIF Conc. μg/ml | $^{125}$IUdR Incorporation (Percent Inhibition) | |
|---|---|---|---|
| | | A549 | CCL 64 |
| TIF-2 | 32 | 55 | 5 |
| | 3.2 | 50 | 9 |
| | 0.32 | 33 | 14 |
| | 0.032 | 8 | 6 |
| TIF-1 | 5.7 | 75 | 78 |
| | 0.57 | 59 | 78 |
| | 0.057 | 37 | 45 |
| | 0.0057 | 0 | 23 |

TIF-2 and TIF-1 were both derived from concentrated conditioned media from the human rhabdomyosarcoma line, A673. TIF-2 partially purified by Bio-Gel P-100 and CM-cellulose chromatography. TIF-1 was partially purifier by Bio-Gel P-100 chromatography. Test cells were human adenocarinoma of the lung, A549, and normal mink lung cells, CCL 64. Inhibition is expressed as percent of control ($^{125}$IUdR incorporation) as in Tumor Inhibitory Assay.

PROPERTIES DISTINGUISHING TIF-1 FROM TIF-2

TIF-1 as described herein supra, is isolated from the 10,000–16,000 molecular weight region of a Bio-Gel P-100 column. The region of TIF-2 activity is found at 18–22,000 $M_r$.

Both TIF-1 and TIF-2 inhibit the growth of a number of human tumor cells tested in soft agar and monolayer culture as listed above. The sensitivity of tumor cells to inhibition by the TIFs, however, varies depending upon cell type, cell passage in tissue culture, and the class of TIF used. In monolayer cultures both TIFs stimulate normal human fibroblasts and normal human embryonic kidney cells.

Both TIFs are acid and heat stable low molecular weight factors which are concentration-dependent in their activity. The inhibitory activity of TIF is reversible if the factor is removed from the cells within one hour after treatment. TIF-1 is trypsin sensitive while TIF-2 is not, although it is presumed to be a protein because of its molecular weight and its many similar characteristics to TIF-1.

Both TIF-1 and TIF-2 can inhibit the growth of A673 cells, the source from which they were derived. This tumor line produces transforming growth factors (TGFs) and at least two kinds of tumor inhibiting factors which may work antagonistically to control tumor growth.

A summary of some of the distinguishing characteristics of TIF-1 and TIF-2 is listed in Table 9.

TABLE 9

Summary - characteristics of TIF-2 and TIF-1.

| | TIF-2 | TIF-1 |
|---|---|---|
| Interferon activity | − | − |
| Heat stability 56° C. 30′ | + | + |
| 100° C. 3′ | partially unstable | + |
| Trypsin sensitivity | − | + |
| Human tumor inhibition | + | + |
| Fibroblast stimulation | + | + |
| Mink lung cell inhibition | − | + |
| Mitogenic activity | + | + |
| Molecular weight* | 18–22,000 | 10–16,000 |
| Elution from μBondapak C$_{18}$ column Acetonitrile gradient | 38–42% | 28–33% |

*Approximate molecular weight determined by elution from a Bio-Gel P-100 column.

Among various uses of the TIFs of the present invention, of course, preparations such as pharmaceutical compositions comprising tumor inhibiting or normal-cell-growth-stimulating amount of TIFs and pharmaceutically) acceptable carrier and adjuvant are included. Such pharmaceutical compositions can be prepared using processes well known in the art. Also included among the utilities of the substance of the present invention are methods of inhibiting growth of tumor cells comprising administering to a host having or inflicted with susceptible tumor, a tumor inhibiting amount of the substance. Any mode, and form of administering the substance, e.g. as tablet, solution, suspension, paste, intraperitoneally, subcutaneously and the like could be employed. Suitable vehicles, e.g. physiological saline, etc., well known in the art could also be used. A method of wound healing comprising administering or applying the TIFs in a wound-healing amount to a wound is also included in accordance with the present invention.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. Substantially pure polypeptide tumor growth inhibitory factor 1 having the property of inhibiting tumor cell growth without inhibiting TGF-dependent growth of normal rat kidney NRK-49F cells in soft agar and without having antiviral effect, further having the properties of;

(a) being stable to 1M acetic acid at 4 ° C.;
    (b) being stable at about 56° C. when exposed for about 30 minutes;
    (c) being inhibitory to CCL-64 normal mink lung cells; and
    (d) being stimulatory to growth of normal human fibroblasts.

2. Substantially pure polypeptide tumor growth inhibitory factor 2 having the property of inhibiting tumor cell growth without inhibiting TGF-dependent growth of normal rat kidney NRK-49F cells in soft agar and without having antiviral effect, further having the properties of:
(a) being table to 1 M acetic acid at 4° C.;
(b) being stable at about 56° C. when exposed for about 30 minutes;
(c) being non-inhibitory to CCL-64 normal mink lung cells; and
(d) being stimulatory to growth of normal human fibroblasts.

* * * * *